United States Patent [19]

Desmond et al.

[11] Patent Number: 4,801,569

[45] Date of Patent: Jan. 31, 1989

[54] NOVEL FIXED-BED VANADIUM PHOSPHATE CATALYST SYSTEMS

[75] Inventors: Michael J. Desmond, Cleveland Heights; Marc A. Pepera, Northfield Center, both of Ohio

[73] Assignee: The Standard Oil Company, Cleveland, Ohio

[21] Appl. No.: 792,714

[22] Filed: Oct. 30, 1985

[51] Int. Cl.$^4$ .................. B01J 27/198; B01J 21/02
[52] U.S. Cl. .................................. 502/209; 502/202
[58] Field of Search ........................... 502/209, 202

[56] References Cited

U.S. PATENT DOCUMENTS

| | | | |
|---|---|---|---|
| 3,288,721 | 11/1966 | Kerr | 502/209 |
| 3,474,041 | 10/1969 | Kerr | 252/411 |
| 3,493,517 | 2/1970 | Jaffe | 502/211 |
| 4,020,174 | 4/1977 | Partenheimer | 252/415 |
| 4,062,873 | 12/1977 | Harrison | 307/60 |
| 4,064,070 | 12/1977 | Harrison | 27/14 |
| 4,070,379 | 1/1978 | Ciquier et al. | 502/209 X |
| 4,123,442 | 10/1978 | Bakshi | 307/60 |
| 4,132,670 | 1/1979 | Katsumoto et al. | 27/18 |
| 4,151,116 | 4/1979 | McDermott | 27/14 |
| 4,171,316 | 10/1979 | Pedersen | 307/60 |
| 4,187,235 | 2/1980 | Katsumoto et al. | 307/60 |
| 4,220,595 | 9/1980 | Dickinson et al. | 502/209 X |
| 4,244,878 | 1/1981 | McDermott | 307/60 |
| 4,288,372 | 9/1981 | Hutchings et al. | 307/60 |
| 4,292,201 | 9/1981 | Vartuli et al. | 502/209 |
| 4,333,853 | 6/1982 | Milberger et al. | 27/18 |
| 4,350,611 | 9/1982 | Lemanski et al. | 27/14 |
| 4,371,702 | 2/1983 | Bither, Jr. | 307/60 |
| 4,442,226 | 4/1984 | Bither, Jr. | 27/14 |
| 4,454,245 | 6/1984 | Robinson et al. | 502/209 |
| 4,455,388 | 6/1984 | Robinson et al. | 502/209 |
| 4,562,269 | 12/1985 | Moorhead | 502/209 X |

*Primary Examiner*—H. M. S. Sneed
*Assistant Examiner*—William G. Wright
*Attorney, Agent, or Firm*—Michael F. Esposito; David J. Untener; Larry W. Evans

[57] ABSTRACT

A novel system for the preparation of maleic anhydride by catalytic oxidation of a hydrocarbon such as butane wherein the catalyst system comprising a mixture of (1) a mixed vanadium-phosphate catalyst and (2) a noncatalytic material comprising an oxide of a Group IA–IIIA element, Pb, In, Sb, Sn, Tl, Bi or mixtures thereof.

16 Claims, No Drawings

NOVEL FIXED-BED VANADIUM PHOSPHATE CATALYST SYSTEMS

BACKGROUND OF THE INVENTION

The present invention relates to the preparation of maleic anhydride by catalytic oxidation of butane. In particular, the present invention is directed to improving the lifetime of the catalyst used during the production of maleic anhydride by catalytic oxidation of butane. In addition, the present invention is directed to a novel catalyst system comprising an intimate mixture of component containing a catalytic material and a component containing noncatalytic material capable of extending the lifetime of the catalyst.

Maleic anhydride is a commercially available chemical having significant utility throughout the world. It can be used alone or with other acids in the manufacture of alkyl and polyester resins. It is a versatile chemical intermediate also useful as a monomer to produce various copolymers such as the copolymers of maleic anhydride and vinyl acetate. Significant quantities of maleic anhydride are produced each year to satisfy these needs.

Typically, maleic anhydride can be produced by oxidizing hydrocarbons such as butane, butene, 1,3-butadiene and benzene. The oxidation is carried out in the presence of an oxidation catalyst. Vanadium-phosphate catalysts having the general formula $V_aP_bO_x$ are especially active to catalyze the vapor phase oxidation of hydrocarbons to maleic anhydride. For example, the high surface area catalyst described in U.S. Pat. No. 4,123,442 have been utilized in the oxidation of butane to maleic anhydride. In addition, promoted vanadium phosphate catalysts such as those described in U.S. Pat. No. 4,371,702 have also been utilized in the production of maleic anhydride from butane. In general, these catalyst comprised of vanadium, phosphorus and oxygen, have an intrinsic surface area in the range of about 7-60 square meters per gram, a phosphorus to vanadium atomic ratio in the range of 0.9-1.8:1 and an average vanadium valence in the range of 3.9 to 4.6.

The oxidation process is usually carried out in a fixed bed and the catalyst is contacted with a hydrocarbon under reducing conditions. Typically, the oxidation is carried out at about 300°-500° C. In practice, the oxidation feed is fed to a fixed bed tube reactor containing the catalyst material. Shortly after the hydrocarbon is introduced into the reactor, it begins to oxidize rapidly and creates a hot spot in the catalyst bed. As the time of reaction on the catalyst increases, the activity and selectivity of the catalyst decreases. This is generally termed catalyst aging. As the catalyst ages, the selectivity of the catalyst to maleic anhydride drops precipitously while total conversion of the butane remains constant or increases. When the selectivity to maleic anhydride drops below the acceptable level, the catalyst must either be replaced or regenerated. For examples of typical catalyst regeneration, see U.S. Pat. Nos. 4,020,174; 4,123,442; 4,081,460; 4,006,168 and reissue Patent No. 0030430.

While regeneration of the catalyst is a viable alternative to replacement, it should be highly desirable to increase the lifetime of the catalyst so that regeneration can be delayed as long as possible. Applicants have found a relatively simple and economical procedure for increasing the lifetime of such catalyst without affecting the selectivity of the catalyst to the production of maleic anhydride.

SUMMARY OF THE INVENTION

The primary object of the present invention is to provide a novel catalyst system for use in the production of maleic anhydride.

It is another object of the present invention to provide a process for extending the life of a mixed vanadium-phosphate catalyst used in the production of maleic anhydride.

It is a further object of the present invention to provide an improved procedure for the catalytic oxidation of a hydrocarbon to maleic anhydride in a fixed bed reactor.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the catalyst system of the present invention for use in the catalytic oxidation of a hydrocarbon to maleic anhydride comprises an intimate mixture of (1) a component containing an active catalytic material characterized by the formula:

$$A_xV_yP_zO_w$$

wherein

A comprises an alkali metal, alkaline earth metal, a transition metal, Group IIIB element, IVB element, VB element or mixtures thereof;

x=0 to about 1;

y=about 1;

z=0.8 to 2.5; and w=the number of oxygen atoms sufficient to satisfy the valence requirements of the other elements; and (2) a component containing a noncatalytic material comprising an oxide of a Group IA-IIIA element, Pb, In, Sb, Sn, Tl, Bi or mixtures thereof. Preferably, the two materials are utilized in particulate form.

Preferably, the noncatalytic material is an oxide selected from the group consistig of Group IIA, IIIA, and Sb, Bi. Most preferably, the oxide is selected from the group consisting of Mg, La, Sb and Bi.

In accordance with another aspect of the present invention as embodied and broadly described herein, the process for improving the lifetime of a promoted or nonpromoted vanadium-phosphate catalyst useful in the production of maleic anhydride from a hydrocarbon comprises mixing together the catalytic containing component and the noncatalytic containing component as defined above to form an intimate mixture of the two components.

In accordance with a still further aspect of the present invention, the process according to the present invention for the production of maleic anhydride by the catalytic oxidation of a hydrocarbon comprises oxidizing the hydrocarbon with molecular oxygen in the presence of a catalyst system comprising an intimate mixture of (1) a component containing an active catalytic material characterized by the formula:

$$A_xV_yP_zO_w$$

wherein
A comprises an alkali metal, alkaline earth metal, a transition metal, Group IIIB element, IVB element, VB element or mixtures thereof;
x=0 to about 1;
y=about 1;
z=0.8 to 2.5; and
w=the number of oxygen atoms sufficient to satisfy the valence requirements of the other elements; and (2) a noncatalytic material comprising an oxide of a Group IA-IIIA element, Pb, In, Sb, Sn, Tl, Bi or mixtures thereof.

The particular advantages of the present invention in comparison with the previously described catalyst are that (1) the catalyst system of the present invention improves catalyst lifetime and (2) improves catalyst resistance to thermal shock caused by hot spots in the fixed bed reactor. The thermal shock resistance of the catalyst system of the present invention alleviates some of the concerns attendant with the start-up procedures of other vanadium-phosphate catalysts. That is, careful attention has been necessary previously in other catalyst start-up processes to ensure that the thermal reaction in the reactor does not proceed so rapidly as to destroy the catalyst in the bed. Applicants' catalyst system exhibits improved resistance to destruction from thermal shock thereby greatly facilitating start-up procedures. Obviously, these two advantages representative a significant economic advantage over the procedures set forth previously.

DETAILED DESCRIPTION OF THE INVENTION

In the process of the present invention, a hydrocarbon is oxidized with molecular oxygen or an oxygen containing gas in the vapor phase in the presence of a catalyst to produce maleic anhydride. In particular, the process of the present invention comprises contacting the hydrocarbon in the vapor phase with a mixed vanadium-phosphate catalyst in the presence of an oxygen containing gas to produce maleic anhydride.

The hydrocarbon reacted to form maleic anhydride may be n-butane, n-butenes, 1,3 butadiene or mixtures thereof. Most preferably, the hydrocarbon is n-butane or a mixture of hydrocarbons that are produced in a refinery stream. The molecular oxygen needed for the reaction to produce maleic anhydride is most conveniently added as air, but synthetic streams containing molecular oxygen also may be utilized. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to hydrocarbon may range from about 2 to 30 moles of oxygen per mole of hydrocarbon. Preferably, the oxygen/hydrocarbon ratio is about 4 to about 20 moles of oxygen per mole of hydrocarbon.

The reaction temperature may also vary and is dependent upon the particular hydrocarbon and catalyst employed. Normally, temperatures of between 100° C. to about 600° C. are employed with preferably between 250° C. and 600° C. being preferred. Most preferably, temperatures of between 350° C. to 450° C. are utilzied.

The contact time for the reaction may be as low as a fraction of a second (e.g. 0.5) to as high as 50 seconds. In addition, the reaction may be conducted at atmospheric, superatmospheric or subatmospheric pressure.

The novel catalyst system of the present invention used in the catalytic oxidation of the hydrocarbon to maleic anhydride comprises a mixture of (1) a component containing an active catalytic material characterized by the formula:

$$A_xV_yP_zO_w$$

wherein
A, x, y, z and w are defined as previously set forth in the application, and (2) a component containing a noncatalytic material (scavenging phase) comprising an oxide of a Group IA element, Group IIA element, Group IIIA element, Pb, In, Sb, Sn, Tl, Bi or mixtures thereof. Preferably, z may vary from 1.0 to 1.2.

The catalyst component of the system may be used alone or a support could be employed. Suitable supports include silica, alumina, silica-alumina, low surface area alumina such as Alundum, silicon carbide, titania, boron phosphate, zirconia, and the like. It is essential to the present invention that the vapors present in the reactor contact directly the noncatalytic material of the catalyst system. Accordingly, the support material for the catalytic material of the catalyst system is not sufficient to produce the results achieved in the present invention because the support material is entrained in the catalytic phase. The noncatalytic material must be a separate, physically distinct component of the catalyst system and the support for the catalyst material should not be considered for purpose of this invention as being separate from the active catalyst material.

Conventional vanadium-phosphate catalysts known for use in the production of maleic anhydride may be utilized in the present invention. Typically, catalysts as described in U.S. Pat. Nos. 4,350,611 and 4,333,853 are suitable for practice of the present invention. The preparation and composition of these catalysts as set forth in the above-identified patents are herein incorporated by reference.

The noncatalytic material or scavenging component of the catalyst system is made by mixing a metal compound, typically a salt of the selected metals such as a nitrate, with a carrier support material such as those defined above. For example, Ludox AS-40 silica sol has been utilized to provide the inert support from the metal oxide scavenging component of the catalyst system. In addition, alundum is another support suitable for the metal oxide component of the catalyst system. Other conventional supports such as silicon carbide, titania, alumina, etc. may be utilized in the practice of the present invention. Generally the metal compound(s) on the inert support is dried and then calcined at a temperature of between 350° C. thru to 900° C. for between about 2 to 8 hours to obtain the metal oxide coating on the inert support.

The resulting noncatalytic or scavenging component of the catalyst system is then mixed with the catalyst material of the system to produce a mixture which contains between 1 and 10 weight % of noncatalytic material producing a catalyst system having two distinct and separate components. Preferably, the distinct and separate components are mixed together in particulate form producing an intimate mixture of catalytic and noncatalytic particles. It should be understood that the amount of noncatalytic material utilized in the catalyst system may vary according to the results desired. However, the noncatalytic or scavenging component should be present in an amount which will extend the lifetime of the catalytic component and not affect substantially the selectivity and conversion rates of the catalytic material in the production of the maleic anhydride. Preferably, 5 weight % and as low as 2.5 weight % of the scavenging or noncatalytic material may be utilized in the practice of the present invention.

The mixing of the two distinct materials of the catalyst system of the present invention may be done by conventional means. Typically, the particulate catalyst material and the noncatalyst material in particulate form are mixed by stirring in a suitable container. There is no criticality as to how the materials are mixed but the components should be stirred until an intimate blend of the two components is obtained.

In accordance with another aspect of the present invention as embodied and broadly described herein, the process for improving the lifetime of a mixed vanadium-phosphate catalyst used for the production of maleic anhydride from n-butane comprises mixing a first component containing a catalytic material comprising a mixed vanadium-phosphate catalyst with a second component containing a noncatalytic material comprising a metal oxide selected from the group consisting of Group IA-IIIA elements, Pb, In, Sb, Sn, Tl, Bi and mixtures thereof. It should be understood that the periodic table of elements used by applicants in designating the particular elements by group is the IUPAC Periodic Table. Most preferably, the noncatalytic material of the catalyst system comprises elements selected from the group consisting of Group IIA, IIIA, Sb and Bi. Especially preferred are the metal oxides selected from the group of Sb, Mg, La and Bi.

To further illustrate the process of the present invention, the following examples are presented.

EXAMPLES 1-8

Catalyst Material

In each of these examples the catalytic material of the catalyst system of the present invention comprised a vanadium-phosphate base oxidation catalyst with a 1:1 vanadium:phosphorus ratio wherein the vanadium possessed an average oxidation state between about 3.8 to 4.4. The catalysts were prepared according to the procedure set forth in U.S. Pat. No. 4,333,853 to Milberger et al. assigned to the assignees of the instant application are herein incorporated by reference.

Noncatalytic (Scavenger) Material Preparation

A metal compound was mixed with a sufficient quantity of Ludox AS-40 silica sol so as to obtain a product consisting of 20 weight % metal, with the balance being silica and associated oxide. These materials were dried, calcined at 450° C. (4 hours), followed by a high temperature calcination at 900° C. for 2 hours. Nitrate salts were used as the precursors for Fe, Cu, Zn, La, Mg and Bi containing materials, with antimonous oxide used for the Sb containing material. Additionally, a "blank" was prepared using silica sol only. The surface areas of the calcined metal oxide materials were as follows: Cu/Silica, 28 $m^2/gm$; Fe/Silica, 85 $m^2/gm$; La/Silica, 53 $m^2/gm$; Mg/Silica, 46 $m^2/gm$; Zn/Silica, 50 $m^2/gm$; Sb/Silica, 48 $m^2/gm$; Bi/Silica, 1 $m^2/gm$; and Silica 4 $m^2/gm$.

The resulting catalytic and noncatalytic materials were mixed to form the catalyst system of the present invention. The catalyst system contains 10 weight % noncatalytic material and 90 weight % catalytic material.

Five grams of the combined system was loaded into a fixed bed reactor for evaluation. The activity/selectivity results for the conversion of butane to maleic anhydride appear in Table I set forth below. As can be seen, the transition metal containing materials had an adverse effect on catalyst performance. Accordingly, the transition metal oxides are not suitable for the practice of the present invention. The preferred metal compounds are the oxides of La, Mg, Bi and Sb.

TABLE 1

| Example | Temp. °C. | Contact Time Sec. | % $O_2$ in Effluent | % PPC CO | % PPC $CO_2$ | % PPC n-$C_4$ | % PPC Maleic | % SEL CO | % SEL $CO_2$ | % SEL Maleic | % Total Convers. |
|---|---|---|---|---|---|---|---|---|---|---|---|
| 1 AS-40/— | 400 | 0.7 | 16.6 | 14.8 | 17.5 | 29.7 | 38.0 | 21.0 | 24.9 | 54.1 | 70.3 |
| 2 AS-40/Zn | 400 | 0.7 | 15.6 | 23.7 | 30.0 | 28.4 | 17.9 | 33.1 | 41.9 | 25.0 | 71.6 |
| 3 AS-40/Mg | 400 | 0.7 | 16.8 | 16.3 | 16.9 | 26.7 | 40.1 | 22.3 | 23.0 | 54.7 | 73.3 |
| 4 AS-40/La | 400 | 0.7 | 17.0 | 15.4 | 17.2 | 30.4 | 37.0 | 22.2 | 24.7 | 53.2 | 69.6 |
| 5 AS-40/Fe | 400 | 0.7 | 16.4 | 18.8 | 24.1 | 27.7 | 29.4 | 26.0 | 33.3 | 40.7 | 72.3 |
| 6 AS-40/Cu | 400 | 0.7 | 14.2 | 22.5 | 53.2 | 24.3 | 0.0 | 29.8 | 70.2 | 0.0 | 75.7 |
| 7 AS-40/Sb | 400 | 0.7 | 16.9 | 15.7 | 16.6 | 28.7 | 39.0 | 22.0 | 23.3 | 54.6 | 71.3 |
| 8 AS-40/Bi | 400 | 0.7 | 17.0 | 15.2 | 19.1 | 27.8 | 37.9 | 21.0 | 26.4 | 52.5 | 72.2 |

EXAMPLES 9-14

The following samples were prepared in substantially the sample manner described previously for Examples 1-8. However, the run temperature for each sample was 425° C. The results are set forth below in Table 2 and again demonstrate that transition metal oxides (Fe) adversely affect catalyst performance and are not suitable in the practice of the present invention.

TABLE 2

| Example | Temp. °C. | Contact Time Sec. | % $O_2$ in Effluent | % PPC CO | % PPC $CO_2$ | % PPC n-$C_4$ | % PPC Maleic | % SEL CO | % SEL $CO_2$ | % SEL Maleic | % Total Convers. |
|---|---|---|---|---|---|---|---|---|---|---|---|
| 9 AS-40/— | 425 | 0.68 | 15.0 | 21.1 | 24.6 | 12.9 | 41.4 | 24.2 | 28.3 | 47.6 | 87.1 |
| 10 AS-40/Mg | 425 | 0.68 | 14.9 | 24.7 | 26.8 | 8.8 | 39.7 | 27.1 | 29.4 | 43.5 | 91.2 |
| 11 AS-40/La | 425 | 0.68 | 14.9 | 23.2 | 30.5 | 10.9 | 35.4 | 26.0 | 34.2 | 39.8 | 89.1 |
| 12 AS-40/Fe | 425 | 0.68 | 13.9 | 28.9 | 42.6 | 8.6 | 19.9 | 31.6 | 46.6 | 21.8 | 91.4 |
| 13 AS-40/Sb | 425 | 0.68 | 15.2 | 24.1 | 24.3 | 9.1 | 42.5 | 26.5 | 26.7 | 46.8 | 90.9 |
| 14 AS-40/Bi | 425 | 0.68 | 14.8 | 23.0 | 32.8 | 9.0 | 35.2 | 25.3 | 36.0 | 38.7 | 91.0 |

EXAMPLE 15

A life test was run with Sb/Silica as the scavenging or noncatalytic material together wtih the VPO catalyst having the formula $V_{1.0}P_{1.0}O_x$ and prepared by the procedure described in general in U.S. Pat. No. 4,333,853. The results of this test are set forth below in Tables 3 and 4 and are compared to the base results obtained with a VPO catalyst having the same formula without the scavenging component present. In order to determine the effects of adverse conditions on the scavenging containing systems, these systems were run under more strenuous conditions of temperature at the "hot spot" and butane throughput. Additionally, early in the test of the 2.5% (20% Sb/Silica) containing system a thermal upset allowed the "hot spot" temperature to surge past the undesirable 500° C. mark. Throughout both life tests the temperature was adjusted in order to maintain a steady hot spot temperature. Despite these handicaps, the scavenger containing systems compared favorably to the catalyst containing no scavenger component. Table 3 contains comparison data through the first 1000 hours for the fixed bed catalytic runs. Particularly noteworthy is the steady decline in the base case selectivity (values are in % change of selectivity of the butane converted to maleic anhydride), versus the near random fluctuations for the system with the antimony containing component. Table 4 shows the comparative conversion and selectivity to maleic anhydride of the two systems. It is apparent from the results set forth below that although the system of the present invention was run at more adverse conditions, the results obtained were substantially the same as the base system.

TABLE 3

| Example | Time | Change in Selectivity (per hour) | Change in Conversion (percent) | Change in Exotherm (degrees C.) |
|---|---|---|---|---|
| $V_{1.0}P_{1.0}O_x$ w/o Scavenger | 250-350 Hours | 0.007 | −1 | — |
| | 350-500 Hours | −0.005 | +2 | — |
| | 500-600 Hours | −0.070 | +1 | +2 |
| | 600-700 Hours | −0.031 | +1 | +1 |
| | 900-980 Hours | −0.125 | +4 | +14 |
| $V_{1.0}P_{1.0}O_x$ + 2.5% Sb Scavenger | 250-350 Hours | −0.073 | +3 | +7 |
| | 350-500 Hours | −0.012 | — | −2 |
| | 500-600 Hours | 0.046 | — | −3 |
| | 600-700 Hours | −0.079 | +2 | +10 |
| | 700-800 Hours | −0.022 | — | — |
| | 800-900 Hours | +0.030 | +1 | — |
| | 900-980 Hours | −0.017 | +3 | +4 |

TABLE 4

Test conditions and yield by quarters from 0 to 1000 Hours on Stream.

| Example | Exotherm | WWH | Conversion | Selectivity | Grams MA/hr. |
|---|---|---|---|---|---|
| $V_{1.0}P_{1.0}O_x$ w/o Scavenger | 450 | 0.093 | 83 | 60 | 1.48 |
| | 450 | 0.093 | 86 | 56 | 1.43 |
| | 460 | 0.093 | 88 | 48 | 1.25 |
| | 462 | 0.093 | 92 | 45 | 1.27 |
| $V_{1.0}P_{1.0}O_x$ + 2.5% Sb Scavenger | 475 | 0.124 | 76 | 58 | 1.69 |
| | 476 | 0.124 | 78 | 52 | 1.56 |
| | 476 | 0.124 | 80 | 50 | 1.54 |
| | 465 | 0.124 | 77 | 50 | 1.44 |

Without being limited to the following theory, it is postulated that the improved lifetime achieved in the utilization of the catalyst system of the present invention and the resistance to thermal shock when utilizing the scavenging or noncatalytic material in the catalyst system can be attributed to the fact that in a fixed bed operation, hot spots occur in the fixed bed. While the reaction proceeds at the hot spot in the fixed bed, it is believed that either vanadium or phosphorus sublimes from the area of the hot spot and moves slowly through the reactor in the manner of a chromatographic front with the catalyst bed being the stationary material. The vanadium or phosphorus moving through the catalyst material without the addition of the noncatalytic (scavenging component) material will deposit on the cooler catalyst particles away from the hot spot in the bed. This situation produces a surface enriched catalyst which eventually destroys the selectivity of the catalyst to the production of maleic anhydride as the hot spot proceeds down the bed. The presence of the noncatalytic or scavenging component in the catalyst system of the present invention selectively allows the sublimable vanadium or phosphorus to deposit on this component of the catalyst system thereby preventing the catalyst material in the fixed bed from being contaminated with additional vanadium or phosphorus. The scavenging component must selectively take up the vanadium or phosphorus and at the same time not affect the catalytic reaction proceeding in the bed. That is, the selectivity and conversion of the catalyst must not be significantly affected by the presence of the scavenging or noncatalytic material. The catalyst system of the present invention improves the lifetime of the vanadium-phosphate catalyst systems thereby producing significant economic advantages over the previously described catalyst systems.

The foregoing description of the preferred embodiments of the invention have been presented for purposes of illustration and description. They were not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An activated catalyst system comprising a physical mixture containing a first component containing an active catalytic material characterized by the formula:

$$A_xV_yP_zO_w$$

wherein

A comprises an alkali metal, alkaline earth metal, a transition metal, Group IIIB element, IVB element, VB element or mixtures thereof;

x=0 to about 1;

y=about 1;

z=0.8 to 2.5; and w=the number of oxygen atoms sufficient to satisfy the valence requirements of the other elements; and a second component containing a noncatalytic material comprising an oxide of a Group IA-IIIA element, Pb, In, Sb, Sn, Tl, Bi or mixtures thereof.

2. The catalyst system of claim 1 wherein said noncatalytic material comprises an oxide selected from the group consisting of Mg, La, Bi and Sb.

3. The catalyst system of claim 2 wherein said noncatalyst material further comprises an inert support for said oxide.

4. The catalyst system of claim 3 wherein said inert support is selected from the group consisting of silica or a low surface alumina.

5. The catalyst system of claim 1 wherein z equals about 1 to 1.2.

6. The catalyst system of claim 5 wherein x=0 and z=1.0.

7. The catalyst system of claim 1 wherein the weight ratio of the catalyst containing component to the non-catalyst component ranges from 10:1 to 100:1.

8. The catalyst system of claim 6 wherein the ratio is 95:5.

9. The catalyst system of claim 7 wherein the ratio is 97.5:2.5.

10. The system of claim 1 wherein said second component comprises between about 1 to 10 weight percent of said mixture.

11. The system of claim 10 wherein said second component comprising between 2.5 to 5 weight percent of said mixture.

12. A process for improving the lifetime of a mixed vanadium phosphate catalyst useful in the production of maleic anhydride from a hydrocarbon and characterized by the formula $$A_xV_yP_zO_w$$

wherein A comprises an alkali metal, alkaline earth metal, a transition metal, Group IIIB element, IVB element, VB element or mixtures thereof;

x=0 to about 1;

y=about 1;

z=0.8 to 2.5; and w is the number of oxygen atoms sufficient to satisfy the valence requirement of the other elements comprising adding a non-catalytic material comprising an oxide of a Group IA-IIA element, Pb, In, Sb, Sn, Tl, Bi or mixtures thereof to said mixed vanadium phosphate catalyst to form a physical mixture comprising an intimate blend of said catalytic and non-catalytic materials.

13. The process of claim 12 wherein the weight ratio of said catalytic material to said noncatalytic material is between about 10:1 to 100:1.

14. The process of claim 13 wherein said ratio is 95:5.

15. The process of claim 14 wherein said ratio is 97.5:2.5.

16. The process of claim 12 wherein said noncatalytic material is an oxide selected from the group consisting of La, Mg, Bi and Sb.

* * * * *